(12) United States Patent
Zhang et al.

(10) Patent No.: US 7,632,567 B1
(45) Date of Patent: Dec. 15, 2009

(54) MICRONIZED WOOD PRESERVATIVE FORMULATIONS COMPRISING COPPER AND ZINC

(75) Inventors: Jun Zhang, Getzville, NY (US); Wenjin Zhang, Tonawanda, NY (US)

(73) Assignee: Osmose, Inc., Buffalo, NY (US)

( * ) Notice: Subject to any disclaimer, the term of this patent is extended or adjusted under 35 U.S.C. 154(b) by 29 days.

(21) Appl. No.: 11/849,082

(22) Filed: Aug. 31, 2007

Related U.S. Application Data

(60) Provisional application No. 60/824,117, filed on Aug. 31, 2006.

(51) Int. Cl.
*B32B 5/66* (2006.01)
(52) U.S. Cl. .................. 428/323; 428/328; 428/528; 428/535; 428/537.1; 428/403; 424/78.09; 106/18.32; 427/298
(58) Field of Classification Search ............... 428/323, 428/328, 528, 535, 537.1; 424/78.09; 106/18.32; 427/298
See application file for complete search history.

(56) References Cited

U.S. PATENT DOCUMENTS

| | | | |
|---|---|---|---|
| 1,388,513 A | 8/1921 | Chandler | |
| 1,999,458 A | 4/1935 | Hollister | |
| 3,007,844 A | 11/1961 | Schultz et al. | |
| 3,816,307 A | 6/1974 | Woods | |
| 3,945,835 A | 3/1976 | Clarke | |
| 3,968,276 A | 7/1976 | Allen | |
| 4,058,607 A | 11/1977 | Hennart | |
| 4,062,991 A | 12/1977 | Kyte | |
| 4,142,009 A | 2/1979 | Kyte et al. | |
| 4,310,590 A | 1/1982 | Petigara | |
| 4,313,976 A | 2/1982 | Leach | |
| 4,622,248 A | 11/1986 | Leach | |
| RE32,329 E | 1/1987 | Paszner | |
| 4,649,065 A | 3/1987 | Hein | |
| 4,663,364 A | 5/1987 | Iwasaki | |
| 4,741,971 A | 5/1988 | Beck | |
| 4,897,427 A | 1/1990 | Barnavon et al. | |
| 4,923,894 A | 5/1990 | Kanda | |
| 4,935,457 A * | 6/1990 | Metzner et al. | ............ 524/14 |
| 5,196,407 A | 3/1993 | Goletz | |
| 5,246,652 A * | 9/1993 | Hsu et al. | ............ 264/109 |
| 5,277,979 A | 1/1994 | Kielbania, Jr. | |
| 5,304,376 A | 4/1994 | Friedrichs | |
| 5,342,438 A | 8/1994 | West | |
| 5,424,077 A | 6/1995 | Lajoie | |
| 5,426,121 A * | 6/1995 | Bell | ............ 514/500 |
| 5,438,034 A | 8/1995 | Walker | |
| 5,462,589 A | 10/1995 | Nicholas | |
| 5,484,934 A | 1/1996 | Ikeda et al. | |
| 5,527,384 A | 6/1996 | Williams et al. | |
| 5,536,305 A | 7/1996 | Yu | |
| 5,552,378 A | 9/1996 | Trinh | |
| 5,635,217 A | 6/1997 | Goettsche | |
| 5,667,795 A | 9/1997 | Fraley | |
| 5,714,507 A | 2/1998 | Valcke | |
| 5,763,364 A | 6/1998 | Frisch et al. | |
| 5,833,741 A | 11/1998 | Walker | |
| 5,874,025 A * | 2/1999 | Heuer et al. | ............ 252/383 |
| 5,874,476 A | 2/1999 | Hsu | |
| 5,879,025 A | 3/1999 | Blumenthal | |
| 5,972,266 A | 10/1999 | Fookes | |
| 5,990,043 A | 11/1999 | Kugler et al. | |
| 6,110,263 A | 8/2000 | Goettsche et al. | |
| 6,123,756 A | 9/2000 | Poppen | |
| 6,274,199 B1 * | 8/2001 | Preston et al. | ............ 427/298 |
| 6,306,202 B1 | 10/2001 | West | |
| 6,352,583 B1 | 3/2002 | Goettsche et al. | |
| 6,482,814 B1 | 11/2002 | Bath | |
| 6,485,790 B2 | 11/2002 | Walker | |
| 6,503,306 B1 | 1/2003 | Watkins | |
| 6,514,512 B1 | 2/2003 | Puterka et al. | |
| 6,521,288 B2 | 2/2003 | Laks et al. | |
| 6,541,038 B1 | 4/2003 | Tanaka et al. | |
| 6,558,685 B1 | 5/2003 | Kober et al. | |
| 6,576,661 B1 | 6/2003 | Bruck et al. | |
| 6,585,989 B2 | 7/2003 | Herbst et al. | |
| 6,753,035 B2 | 6/2004 | Laks et al. | |

(Continued)

FOREIGN PATENT DOCUMENTS

CA 2103470 8/1994

(Continued)

OTHER PUBLICATIONS

Superior Court of New Jersey, Decision After Trial, Phibro-Tech, Inc. v. Osmose Holding, Inc. Jun. 25, 2007.

(Continued)

*Primary Examiner*—Leszek Kiliman
(74) *Attorney, Agent, or Firm*—Milbank, Tweed, Hadley & McCloy LLP

(57) ABSTRACT

Use of micronized zinc compounds in wood preservation treatments containing micronized copper compounds significantly increases the efficacy of the treatment with respect to that of the copper compounds alone. Micronized copper compounds used at a retention in the range of from 0.005 to 1 pounds per cubic foot (pcf) expressed as CuO equivalent, and zinc compounds are used at a retention in the range of from 0.005 to 1 pcf expressed as ZnO equivalent, the increase in wood preservation efficacy over similar retentions of copper compounds alone can be seen in as little as 24 months.

21 Claims, No Drawings

U.S. PATENT DOCUMENTS

| | | |
|---|---|---|
| 6,849,276 B1 | 2/2005 | Dufau |
| 6,905,531 B2 | 6/2005 | Richardson et al. |
| 6,905,532 B2 | 6/2005 | Richardson et al. |
| 7,001,452 B2 * | 2/2006 | Zhang et al. ............. 106/18.32 |
| 3,535,423 A1 | 10/2007 | Ordas |
| 7,449,130 B2 | 11/2008 | Lloyd |
| 2002/0051892 A1 * | 5/2002 | Laks et al. .................. 428/541 |
| 2002/0128367 A1 | 9/2002 | Daisey et al. |
| 2004/0258767 A1 | 12/2004 | Leach et al. |
| 2004/0258768 A1 | 12/2004 | Richardson et al. |
| 2004/0258838 A1 | 12/2004 | Richardson et al. |
| 2005/0013939 A1 | 1/2005 | Venden |
| 2005/0107467 A1 | 5/2005 | Richardson et al. |
| 2005/0130866 A1 | 6/2005 | Richardson et al. |
| 2005/0252408 A1 | 11/2005 | Richardson et al. |
| 2005/0255251 A1 | 11/2005 | Hodge |
| 2005/0256026 A1 | 11/2005 | Hodge |
| 2006/0062926 A1 | 3/2006 | Richardson et al. |
| 2006/0075921 A1 | 4/2006 | Richardson et al. |
| 2006/0075923 A1 | 4/2006 | Richardson |
| 2006/0078686 A1 | 4/2006 | Hodge et al. |
| 2006/0086841 A1 | 4/2006 | Richardson et al. |
| 2008/0213608 A1 | 9/2008 | Richardson et al. |

FOREIGN PATENT DOCUMENTS

| | | |
|---|---|---|
| DE | 41 12 652 | 10/1992 |
| EP | 0 472 973 | 3/1992 |
| EP | 1 034 903 | 9/2000 |
| GB | 1 491 330 | 11/1977 |
| JP | S61-244502 | 10/1986 |
| JP | S61-246002 | 11/1986 |
| JP | S62-39201 | 2/1987 |
| JP | S62-116102 | 5/1987 |
| JP | 10-26401 | 1/1989 |
| JP | 10-272610 | 10/1998 |
| JP | 2000-102907 | 4/2000 |
| SE | 379167 | 9/1975 |
| WO | 85/00040 | 1/1985 |
| WO | 00/05955 | 2/2000 |
| WO | 00/24259 | 5/2000 |
| WO | 00/24528 | 5/2000 |
| WO | 00/78281 | 12/2000 |
| WO | 01/91925 | 6/2001 |
| WO | 02/06417 | 1/2002 |
| WO | 03/103392 | 12/2003 |

OTHER PUBLICATIONS

Superior Court of New Jersey Chancery Division, Final Judgment, Phibro-Tech, Inc. v. Osmose Holdings, Inc., Osmose, Inc., Aug. 14, 2007.

Koch, C.C., Synthesis of Nanostructured Materials by Mechanical Milling: Problems and Oppostunities, NanoStructured Materials (1997), vol. 9, pp. 13-22.

Backman, P.A., et al., The Effects of Particle Size and Distribute on Performance of the Fungicide Chlorothalonil, Disease Control and Pest Management, vol. 6, pp. 1242-1245; XP009062911.

Davis, Food Storage and Preservative-Treated Wood, Alaska Science Forum (Mar. 10, 1980) [online] [retrieve on Nov. 10, 2008]. URL:http://www.gi.alaska.edu/Science Forum/ASF3/380.htm/.

STN online, file SCISEARCH, Acc. No. 1993:540390 (Siegfried, Comparative Toxicity of Pyrethroid Insecticides to Terrestrial and Aquatic Insects, Environmental Toxicology and Chemistry (1993), vol. 12, No. 9, pp. 1683-1689). Abstract.

Liu, Y., et al., Use of Nonoparticles for the Controlled Release of Biocides in Pressure-Treated Solid Wood, Polymer Preprints 38(2), 1997, pp. 624-625.

Liu, Y., et al., Use of Nanoparticles for Controlled Release of Biocides in Solid Wood, Journal of Applied Polymer Science, vol. 79, 2001, pp. 458-465.

Lide, D. R., Characteristics of Particles and Particle Dispersoids, CRC Handbook of Chemistry and Physics, 75th Edition, 1994, Florida, CRC Press, pp. 15-38.

Liu, Y., Use of Polymer Nanoparticles as Carriers for the Controlled Release of Biocides in Solid Wood, Dissertation for the Degree of Ph.D. Of Yong Liu, 1999, Michigan Technological University.

International Society of Soil Science (http://clays.org.au/mins.htm).

Hawley's Condensed Chemical Dictionary, 14th Edition, John Wiley & Sons, Inc. 2001, p. 86.

Superior Court of New Jersey, Decision After Trail, *Philrotech Inc.* v. *Osmose Holdings, Inc.* Docket No. C-365-05, Jun. 25m 2007.

Supirior Court of New Jersey Chancery Division, Final Judgement, *Philbrotech, Inc.* v. *Osmose Holdings, Inc.*, Docket No. C-365-05, Aug. 14, 2007.

AWPA Standard E7-01.

AWPA Standard E10-1.

Liu, Y., et al., Michigan Technical Univ. Dept. Chemistry, Houghton, MI, "Use of Polymeric Nanoparticles for Controlled Release of Biocides in Solid Wood", Materials Research Society Symposium Proceedings Series, 1998, vol. 550, Abstract GG3,4.

Shaw, www.fad.gov/ohrms/dockets/ac/01/slides/3736s2_09_shaw.ppt; 2001.

The Merck Index (12th Edition, 1996) Merck & Co., Inc.

* cited by examiner

MICRONIZED WOOD PRESERVATIVE FORMULATIONS COMPRISING COPPER AND ZINC

CROSS-REFERENCE TO RELATED APPLICATIONS

This application claims priority to U.S. Provisional Application No. 60/824,117, filed on Aug. 31, 2006, which is incorporated herein by reference.

FIELD OF THE INVENTION

The present invention relates generally to the field of wood preservatives and more particularly to a wood preservative composition comprising micronized particles of copper compounds and zinc compounds.

BACKGROUND OF THE INVENTION

Wood preserving compositions are well known for preserving wood and other cellulose-based materials such as paper, particleboard, textiles, rope, etc., against organisms, including fungi and insects, responsible for the destruction of wood. Many conventional wood preserving compositions contain copper amine complexes. Copper amine complexes have been used in the past because the amine solubilizes the copper in aqueous solutions. The copper in such copper amine complexes is obtained from a variety of copper bearing materials, such as copper scrap, cuprous oxide, copper carbonate, copper hydroxide, a variety of cuprous and cupric salts, and copper bearing ores. The amine in such copper amine complexes is normally obtained from an aqueous solution of ammonia and ammonium salts, such as ammonium carbonate, and ammonium sulfate, ethanolamines, et cetera. For example, U.S. Pat. No. 4,622,248 describes forming copper amine complexes by dissolving copper (II) oxide [CuO] (also known as cupric oxide) in ammonia in the presence of ammonium bicarbonate.

However, copper ammonia preservatives can affect the appearance of the treated wood giving surface residues and undesirable color. In recent years, many amine-containing compounds, such as the ethanolamines and aliphatic polyamines, have been used to replace ammonia to formulate water-soluble copper solutions. These compounds were chosen because of their strong complexing ability with copper and because they are essentially odorless. U.S. Pat. No. 4,622,248 discloses a method of preparing copper amine complexes by dissolving a mixture of copper (II) carbonate [$CuCO_3$] and copper (II) hydroxide [$Cu(OH)_2$] in ethanolamine and water. The complexing amine (i.e., the ligand) and copper (II) ion combine stoichiometrically and thus the weight ratio of reagents will be different for each complexing amine. However, copper amine based preservatives have higher copper loss due to leaching as compared to traditional copper based preservatives such as chromated copper arsenate (CCA).

Other metal compounds have also been used as biocides in wood and other cellulosic materials. Generally, the metal compounds are used in solution as metal complexes or metal ions. For example, zinc compounds, dissolved in a base, such as ammonia or an acid such as acetic acid solutions have been used in biocidal applications for wood. However, the biocidal efficacy of dissolved zinc compounds has been found to be significantly less than that of copper. Therefore, certain fungi, such as copper-tolerant brown rots, remain difficult to control. Additionally, zinc compounds dissolved in ammonia have a strong odor and pose other environmental/health concerns, and zinc compounds dissolved in acids have a tendency to leach into the environment when used in service. Thus, there continues to be a need for improving the biocidal efficacy of water-based, metal-containing wood preservatives.

SUMMARY OF THE INVENTION

Surprisingly, it has been found that the use of micronized zinc compounds in wood preservation treatments containing micronized copper compounds significantly increases the efficacy of the treatment with respect to that of the copper compounds alone. In particular, when micronized copper compounds are used at a retention in the range of from 0.005 to 1 pounds per cubic food (pcf) expressed as CuO equivalent, and zinc compounds are used at a retention in the range of from 0.005 to 1 pcf expressed as ZnO equivalent, the increase in wood preservation efficacy over similar retentions of copper compounds alone can be seen in as little as 24 months.

The present invention provides compositions for preservation of wood. The compositions comprise micronized particles of copper compounds and micronized particles of zinc compounds. The copper and zinc compound micronized particles can optionally be mixed with a variety of water soluble and/or water insoluble biocides and/or other additives, which may also be present as micronized particles.

The micronized particles of copper and zinc compounds are in the range of 0.001 microns to 25.0 microns. In various embodiments, at least between 50% to 99% of the particles are in the range of 0.001 to 25 microns. In other embodiments, greater than 50 weight % of the particles are in the range of 0.01 to 10 microns, and 0.1 to 1 microns.

This invention also provides a method for using these compositions for preservation of wood. The method comprises the step of contacting a cellulosic material, such as wood, with a composition of the present invention, followed by the impregnation of wood with the composition. Vacuum, vacuum/pressure or dip techniques can be used for effective impregnation. When the compositions of the present invention are used for preservation of wood, there is minimal leaching of the metal or metal compound components from the wood.

DETAILED DESCRIPTION OF THE INVENTION

The term "micronized" as used herein means a particle size in the range of 0.001 to 25 microns. The term "preservative" as used herein means a composition that renders the material to which it is applied more resistant to insect, fungal and microbial attack than the same material without having the composition applied. The term "particle size" refers to the largest axis of the particle, and in the case of a generally spherical particle, the largest axis is the diameter.

The present invention provides wood preservatives comprising micronized copper or copper compounds and micronized zinc or zinc compounds. The compounds of copper and zinc useful for the present invention exhibit low solubility in water, such as for example, a solubility $\leq 1.0$ g per 100 grams of water. Non-limiting examples of suitably insoluble or sparingly insoluble copper compounds include copper carbonate, copper hydroxide, cupric oxide, cuprous oxide, oxine copper, copper borate, copper oxychloride, copper dimethyldithiocarbamate and copper omadine. Non-limiting examples of suitably insoluble or sparingly insoluble zinc compounds include zinc oxide, zinc hydroxide, zinc carbonate, zinc borate and zinc phosphate. In a preferred embodiment, the copper compound is copper carbonate and the zinc compound is zinc oxide. In another preferred embodiment, the copper compound is copper hydroxide and/or copper oxides and the zinc compound is zinc oxide. In additional embodiments, compounds of other metals, micronized or non-micronized, including transition metals (such as the lanthanide and actinide series elements, and tin, cadmium, silver, nickel, etc.) can also be used in addition to copper, zinc and their compounds.

Non-biocidal additives such as water repellants (such as wax emulsions), colorants, emulsifying agents, dispersants, stabilizers, UV inhibitors, enhancing agents (such as trialkylamine oxides and alkoxylated diamines) and the like may also be added to the composition disclosed herein to further enhance the performance of the system or the appearance and performance of the resulting treated products. Those skilled in the art will recognize that some of these agents may also have some biocidal properties.

The micronized copper compounds are used at a retention in the range of from 0.005 to 1 pcf CuO equivalents, and in other embodiments, in the range of from 0.01 to 0.3, and 0.05 to 0.3 pcf CuO equivalents. The micronized zinc compounds are used at a retention in the range of from 0.005 to 1 pcf ZnO equivalents, and in other embodiments, in the range of 0.01 to 0.3, 0.01 to 0.1 pcf ZnO equivalents.

Regardless of the specific compounds used, it is preferred that the weight ratio of elemental copper to zinc is in the range of from about 100:1 to about 1:100; more preferably in the range of from about 10:1 to 1:10, and most preferably in the range of from about 3:1 to about 1:3. In a preferred embodiment, the composition comprises copper carbonate and zinc oxide present in a ratio of 18:1 to 1:18, more preferably in the ratio of 5:1 to 1:5. In another preferred embodiment, the composition comprises copper hydroxide and zinc oxide present in a ratio of 15:1 to 1:15, more preferably 5:1 to 1:5. In another preferred embodiment, the composition comprises cupric and/or cuprous oxide and zinc oxide present in a ratio of 10:1 to 1:10, more preferably in the ratio of 3:1 to 1:3.

In general, the total retention of copper compound and zinc compound in wood is in the range of 0.01 to 2.0 pcf total oxide equivalents, with a preferred range of from 0.01 to 0.5 and more preferred range of from 0.05 to 0.30 total oxide equivalents. The phrase "total oxide equivalents" refers to compounds containing copper and zinc only, and the equivalents are in terms of CuO and ZnO. When wood is to be used in above-ground applications, including without restriction uses such as UC3A and UC3B as listed in the 2005 Book of Standards of the American Wood Preservers Association, it is preferable that the total retention of copper compound and zinc compound be in the range of from 0.02 to 0.12 pcf total oxide equivalents, and when used for other applications, including without restriction uses such as UC4A, UC4B, UC4C, UC5A, UC5B, and UC5C, as listed in the 2005 Book of Standards of the American Wood Preservers Association, it is preferable that the total retention of copper compound and zinc compound be in the range of from 0.10 to 0.40 pcf total metal oxide equivalents.

The size of the micronized particles for the metal compounds is between 0.001 to 25 microns. In various embodiments, the size of at least between 50% to 90% of the particles is between 0.001 to 25 microns, preferably between 0.005 to 10 microns, more preferably between 0.05 to 10 micron and even more preferably between 0.05 to 1.0 microns. For example, in some embodiments, greater than 85, 90, 95, 96, 97, 98 or 99 wt percent particles are in the range of 0.001 to 25 microns, and preferably less than 10 microns, more preferably less than 5 micron and still more preferably, less than 1 micron. It should be understood that although the compositions disclosed herein contain micronized particles, they can contain particles which are not micronized, i.e., with diameters which are outside the range of from 0.001 to 25 microns. For increased likelihood of penetration and uniformity of distribution, it is preferred that at least 50 wt % of the particles should have diameters which are less than 10 microns. More preferred are particle distributions which have at least 65 wt % of the particles with sizes of less than 10 microns. More preferred are particle distributions which have at least 95 wt % of the particles with sizes of less than 1 micron. Particle size distributions which conform to the above size distribution parameters can be prepared by methods known in the art. For example, particles can be obtained by grinding a mixture of biocide and dispersant. The particle size distribution can be controlled by the ratio of dispersant to biocide, grinding times, the size of grinding media, etc. The aforementioned parameters can be adjusted in order to obtain a suitable non-clogging particle distribution.

The micronized particles of the present invention can be prepared through mixing with in dispersants and then go through media grinding. The dispersant can be cationic, non-ionic and anionic, and the preferred dispersants are either non-ionic or cationic. Examples of dispersants are: acrylic copolymers, aqueous solution of copolymers with pigment affinity groups, polycarboxylate ether, modified polyacrylate or modified polyacrylate with groups of high pigment affinity, acrylic polymer emulsions, modified acrylic polymers, poly carboxylic acid polymers and their salts, modified modified poly carboxylic acid polymers and their salts, fatty acid modified polyester, aliphatic polyether or modified aliphatic polyether, solution of polycarboxylate ether, polyetherphosphate, modified maleic anhydride/styrene copolymer, sodium polyacrylate, sodium polymethacrylate, lignin and the like, modified polyether or polyester with pigment affinic groups; fatty acid derivatives; urethane copolymer or modified urethane copolymer, polyetherphosphate, modified maleic anhydride/styrene copolymer, modified polycarboxylic acid or its derivatives, acrylic acid/maleic acid copolymer, polyvinyl pyrrolidone or modified polyvinyl pyrrolidone. Polymeric dispersants are preferred.

The dispersant level is in the range of from about 0.1 to 180% of the weight of the copper and zinc compounds, with a preferred range of 1 to 80%, a more preferred range of 5 to 60%, and still more preferred range of 10 to 30%. The composition can also comprise a defoamer, either a Si-containing defoamer or a non-Si defoamer. The level of the defoamer in the composition is preferably in the range of from about 0.01 to 10% of the weight of the copper and zinc.

The micronized particles can be obtained by grinding compounds using a commercially available grinding mill. Particulate compound can be wet or dry dispersed in a liquid prior to grinding. Alternatively, the non-micronized or micronized copper and zinc compounds can be purchased from commercial sources and ground further to be useful for wood preservation. Other means of obtaining micronized particles include chemical or physical or other mechanical means.

A preferred method of preparing compositions of the present invention is by grinding. One exemplary method involves the formation of a slurry comprising a dispersant, a carrier, and metal compound particles (such as having a particle size in the range of from 1 micron to 500 microns), and optionally, a defoamer. The slurry is transferred to a grinding mill which is prefilled with a grinding media having a size from 0.05 mm to 5 mm, and preferably between 0.1 and 1 mm. The media can be one or more of many commercially available types, including but not limited to steel shots, carbon steel shots, stannous steel shots, chrome steel shots, ceramic (for example, alumina-containing); zirconium-based, such as zirconia, zirconium silicate, zirconium oxide; stabilized zirconia such as stabilized ytz-stabilized zirconia, ceria-stabilized zirconia, stabilized magnesium oxide, stabilized aluminum oxide, etc. The medium preferably occupies 50% to 99% of the grinding chamber volume, with 75 to 95% preferred, and 80 to 90% more preferred. The bulk density of the grinding media is preferably in the range of from 0.5 kg/l to 10 kg/l, and more preferably in the range of from 2 to 5 kg/l. Agitation speed, which can vary with the size of the grinder, is generally in the range of from 1 to 5000 rpm, but can be higher or lower. Lab and commercial grinders generally run at different speeds. A set up which involves a transfer pump which repeatedly cycles the slurry between the mill and a storage tank during grinding is convenient. The transfer pump speed varies from 1 to 500 rpm, and the speeds for lab and commercial grinders can be different. During grinding, defoamer can be added if foaming is observed. During grinding, particle size distribution can be analyzed, and once particle size is within the desired specification, grinding is stopped.

In the preparation of the present composition, the copper and zinc compounds can be mixed together and then ground to result in the desired composition or the copper compounds and the zinc compounds can be ground separately and then mixed together. If they are mixed first and ground together, it is expected that both the copper and the zinc compound micronized particles will show a similar particle size distribution profile. If, however, they are ground first and then mixed, the profiles of the copper and zinc compounds may be similar or different. Therefore, by grinding the copper and zinc compounds separately, compositions comprising different particle size distributions for the two metals can be obtained.

The compositions of the present invention can be a concentrate or a preparation which is ready to apply to wood. It is preferred that the copper compounds and zinc compounds in the concentrated composition be present in a combined weight percent if ground together or individual weight percent if ground separately, in the range of from 1 to 80%, with a preferred weight percent in the range of 5 to 70% and a more preferred weight percent in the range of from 30 to 65%.

The penetration of the dispersion formulation into the cellular structure of the wood or other cellulose-based material is important. If the copper and zinc sources used in formulating the dispersion formulation disclosed herein has a particle size in excess of 25 microns, the particles may be filtered by the surface of the wood and thus may not be uniformly distributed within the cell and cell wall. The primary entry and movement of fluids through wood tissue occurs primarily through the tracheids and border pits. Tracheids have a diameter of about thirty microns. Fluids are transferred between wood cells by means of border pits. The overall diameter of the border pit chambers typically varies from a several microns up to thirty microns while, the diameter of the pit openings (via the microfibrils) typically varies from several hundredths of a micron to several microns. When wood is treated with micronized preservative formulation, if the particle size of the micronized preservative is less than the diameter of the pit openings, a complete penetration and a uniform distribution of micronized preservative in wood is expected. Thus, the compositions of the present invention are formulated so as to provide for effective penetration. Those skilled in the art will recognize that the particle size distributions for a particular application can be adjusted depending upon the need. For example, for application to Southern Pine, it may be preferable to use a composition in which the distribution is skewed toward larger particles within the micronized range, while for other types of wood, such red pine, ponderosa pine, hem fir, cedar, Douglas fir, it may be preferable to use a composition in which the distribution is skewed toward smaller particles within the micronized range.

These compositions are used for treatment of cellulosic material such as wood. The leaching of metal from the treated wood is less for the present compositions than that observed from wood treated with similar non-micronized compositions.

In one embodiment, the method comprises the steps of treating wood with a composition (treating fluid) comprising a dispersion of micronized metal compounds. In another embodiment, wood is treated with a composition comprising a dispersion of micronized metal compounds and organic biocides, wherein the organic biocides are soluble or present as water insoluble micronized particles. The degree of penetration and uniformity of distribution of the particles into the wood cellular structure is related to the prevalence of particles with relatively large particle size. If the significant number of particles are have a particle size in excess of 25 microns, the particles may be filtered by the surface of the wood and thus may not be uniformly distributed within the cell and cell wall. Furthermore, particles with long axes greater than 25 microns may clog tracheids and inhibit the uptake of additional particles. The penetration can be tested generally by AWPA Standard A3-00 "Standard Method for Determining Penetration of Preservatives and Fire Retardants".

The treating fluid may be applied to wood by dipping, soaking, spraying, brushing, or any other means well known in the art. In a preferred embodiment, vacuum and/or pressure techniques are used to impregnate the wood in accord with this invention including the standard processes, such as the "Empty Cell" process, the "Modified Full Cell" process and the "Full Cell" process, and any other vacuum and/or pressure processes which are well known to those skilled in the art.

The standard processes are defined as described in AWPA Standard C1-03 "All Timber Products—Preservative Treatment by Pressure Processes". In the "Empty Cell" process, prior to the introduction of preservative, materials are subjected to atmospheric air pressure (Lowry) or to higher air pressures (Rueping) of the necessary intensity and duration. In the "Modified Full Cell", prior to introduction of preservative, materials are subjected to a vacuum of less than 77 kPa (22 inch Hg) (sea level equivalent). A final vacuum of not less than 77 kPa (22 inch Hg) (sea level equivalent) shall be used. In the "Full Cell Process", prior to introduction of preservative or during any period of condition prior to treatment, materials are subjected to a vacuum of not less than 77 kPa (22 inch Hg). A final vacuum of not less than 77 kPa (22 inch Hg) is used.

The wood preservative compositions of the present invention may comprise optionally one or more organic biocides. In one embodiment, the organic biocide is also present as micronized particles. The organic biocides useful in the present invention can be water soluble as well as water insoluble. Such organic biocides including fungicides, insecticides, moldicides, bactericides, algaecides etc. are well known to those skilled in the art and include triazoles, quaternary ammonium compounds such as alkyldimethylbenzylammonium chloride, dimethyldidecylammonium chloride, dimethyldidecylammonium carbonate/bicarbonate and the like, borate compounds, fluoride compounds and combinations thereof. Water insoluble organic biocides are also well known. Some non-limiting examples of water insoluble organic biocides are described in U.S. patent application publication no. US 2005/0249812 A1, published Nov. 10, 2005, now pending, which is incorporated herein by reference. Preferred organic biocides are azoles, such as, for example, tebuconazole, propiconazole, cyproconazole, simeconazole, 2-(2, 4-difluorophenyl)-1-(1H-1,2,4-triazole-1-yl)-3-trimethylsilyl-2-propanol, and prochloraz. The most preferred azole is tebuconazole. In one embodiment, when the composition of the present invention is used with azoles, such as, for example, tebuconazole, the retention of azole in the wood is in the range of from 0.0001 to 0.5 pcf, with a preferred range of 0.001 to 0.1 pcf, and in other embodiments, in the ranges of from 0.004 to 0.05, or 0.004 to 0.02 pcf.

The following examples are provided to further describe certain embodiments of the invention but are in no way meant to limit the scope of the invention. Examples 1 through 5 demonstrate the formulation of the concentrated dispersions of copper compounds and/or zinc compounds. Examples 6 through 10 demonstrate the preparation of treating fluids using concentrated dispersions for the treatment of wood. Example 11 demonstrates the enhanced wood preservative effect of using zinc and copper together in micronized form.

Example 1

1000 g of copper carbonate and 687.5 g zinc oxide were added to a container containing 1350 grams of water and 337.5 grams of a modified polyacrylate type of dispersant. The mixture was mechanically stirred for 5 minutes and then placed in a grinding mill. The sample was ground for about 30 minutes, and a stable dispersion containing about 50% copper carbonate/zinc oxide was obtained. The particle size of the copper hydroxide dispersion was analyzed by Horiba LA-910 Particle Size Distribution Analyzer (PSDA). The average particle size was 0.29 micrometers (um) with a distribution range of 0.04 um to 1.1 um.

Example 2

1000 g of copper carbonate and 295 g zinc oxide were added to a container containing 836 grams of water and 194 grams of a modified polycarboxylate ether type of dispersant. The mixture was mechanically stirred for 5 minutes and then placed in a grinding mill. The sample was ground for about 25 minutes, and a stable dispersion containing about 60% copper carbonate/zinc oxide was obtained. The particle size of the copper hydroxide dispersion was analyzed by Horiba LA-910 Particle Size Distribution Analyzer (PSDA). The average particle size was 0.25 micrometers (um) with a distribution range of 0.04 um to 0.9 um.

Example 3

2000 g of copper carbonate and 590 g zinc oxide were added to a container containing 1705.0 grams of water and 414.4 grams of an acrylic polymer emulsion type of dispersant. The mixture was mechanically stirred for 10 minutes and then placed in a grinding mill. The sample was ground for about 60 minutes, and a stable dispersion containing about 55% copper carbonate/zinc oxide was obtained. The particle size of the copper hydroxide dispersion was analyzed by Horiba LA-910 Particle Size Distribution Analyzer (PSDA). The average particle size was 0.14 micrometers (um) with a distribution range of 0.04 um to 0.5 um.

Example 4

1000 g copper carbonate was added to a container containing a mixture of 597.0 grams of water, 120.0 grams of a modified poly carboxylic acid polymer type of dispersant and 3.0 g of a defoamer. The mixture was mechanically stirred for 5 minutes and then placed in a grinding mill. The sample was ground for about 30 minutes, and a stable dispersion containing about 27.9 wt % CuO equivalents was obtained. The particle size of the copper carbonate dispersion was analyzed by Horiba LA-910 Particle Size Distribution Analyzer (PSDA). The mean particle size was 0.29 micrometers (um) with about 10% greater than 0.5 microns.

Example 5

1000 g zinc oxide was added to a container containing a mixture of 850 grams of water, 150.0 grams of a modified poly carboxylic acid polymer type of dispersant and 3.0 g of a defoamer. The mixture was mechanically stirred for 10 minutes and then placed in a grinding mill. The sample was ground for about 20 minutes, and a stable dispersion containing about 50% zinc oxide was obtained. The particle size of the copper carbonate dispersion was analyzed by Horiba LA-910 Particle Size Distribution Analyzer (PSDA). The mean particle size was 0.25 micrometers (um) with about 10% greater than 0.5 microns.

Example 6

100 g of the dispersion from Example 1 was mixed with 4900 g of water to produce a preservative treating fluid. The fluid was then used to treat 2"×4"×10" samples of southern pine sapwood, and sealed with epoxy resin, using an initial vacuum of 28" Hg for 15 minutes, followed by a pressure cycle of 135 psi for 25 minutes and a final vacuum of 27" Hg for 10 minutes. The resulting treated wood was weighed and found to have doubled its weight. The treated sample was cut and the cross sections sprayed with a copper indicator to determine copper penetration following the procedure described in American Wood Preservers' Association Standard A3-00, and the blue color indicates the presence of copper. The sample was found to have 100% uniform distribution of copper throughout the cross section.

Example 7

50.0 g of the dispersion from Example 2 were mixed with 3950 g of water to prepare a preservative treating fluid. The product was mixed until uniformly dispersed. A southern pine stake measuring 1.5"×3.5"×10" was placed in a laboratory retort with a vacuum of 27" Hg for 15 minutes. The treating solution was then pumped into the retort and the retort pressurized to 130 psi for 30 minutes. The solution was drained from the retort and the test stake weighed. Based on the weight pickup, the test stake doubled its weight and showed uniform penetration of the cupric oxide throughout the wood cross section. A sample taken from the center portion of the treated wood was submitted for scanning electron microscopy (SEM) analysis.

Example 8

4000 g of treating fluid containing 1.5% carbonate/ZnO and 0.50% didecyldimethylammonium carbonate/bicarbonate was prepared by mixing the dispersion from Example 1 and didecyldimethylammonium carbonate/bicarbonate concentrate. The fluid was used to treat 2"×4"×10" southern pine samples by placing the samples in a chamber and drawing a 27" Hg vacuum for 10 minutes. The treating fluid was then drawn into the chamber and allowed to stay in contact with the wood cubes for 15 minutes. The fluid was pumped from the chamber and the resulting wood had more than doubled its weight. Cross sections of the cubes showed 100% copper penetration. The treated wood was found to control the growth of decay fungi.

Example 9

4000 g of treating fluid containing 1.0% carbonate/ZnO and 0.05% tebuconazole was prepared by mixing the dispersion from Example 2 and a tebuconazole concentrate. The fluid was used to treat 2"×4"×10" southern pine samples by placing the samples in a chamber and drawing a 27" Hg vacuum for 10 minutes. The treating fluid was then drawn into the chamber and allowed to stay in contact with the wood cubes for 15 minutes. The fluid was pumped from the chamber and the resulting wood had more than doubled its weight. Cross sections of the cubes showed 100% copper penetration. The treated wood was found to control the growth of decay fungi.

Example 10

A preservative treating composition was prepared by adding 0.1 kg of dispersion from Example 4, 0.024 kg dispersion from Example 5 and 3.9 kg of water. This fluid was then used to treat full-size lumber using the full-cell process wherein the wood is initially placed under a vacuum of 30" Hg for 30 minutes, followed by the addition of the treating solution. The system was then pressurized for 30 minutes at 110 psi. A final vacuum of 28" Hg for 30 minutes was applied to the wood to remove residual liquid. The wood was found to contain a uniform distribution of copper throughout the cross sections and is resistant to fungal and insect attack.

Example 11

The field performance tests of specific retentions of copper carbonate and zinc oxide were evaluated following the procedure described in American Wood Preservers' Association (AWPA) Standard E7-01: "Standard Method of Evaluating Wood Preservatives by Field Tests with Stakes" (included as "Appendix I"). The rating system for decay grades are described as follows:

Decay Grades:

10 = Sound, suspicion of decay permitted
9 = Trace decay to 3% of cross section
8 = Decay from 3 to 10% of cross section
7 = Decay from 10 to 30% of cross section
6 = Decay from 30 to 50% of cross section
4 = Decay from 50 to 75% of cross section
0 = Failure due to fungal decay The data in the table below demonstrates the unexpected efficacy of using copper and zinc compounds in combination in the retention ranges of the present invention. Note that the replacement of a portion of the copper oxide equivalent with approximately the same zinc oxide equivalent gives a significant rise in wood preservation efficacy. (Compare point 4 with point 5, and point 1 with point 7 below.)

TABLE 1

| Preservative System | RETENTION, PCF, A.I. | 8 MONTHS | 20 MONTHS | 32 MONTHS | 44 MONTHS |
| --- | --- | --- | --- | --- | --- |
| Average Decay Ratings of Cu and Cu—Zn Preservative Treated Wood Stakes installed in Gainesville, FL | | | | | |
| 1) Cu alone System | 0.065 CuO | 10.0 | 6.6(3) | 4.3(5) | 0.9 |
| 2) Cu alone System | 0.12 CuO | 10.0 | 9.8 | 7.5(2) | 2.5 |
| 3) Cu alone System | 0.19 CuO | 10.0 | 8.9(1) | 8.5(1) | 6.3(3) |
| 4) Cu alone System | 0.25 CuO | 10.0 | 10.0 | 8.9(1) | 6.6(3) |
| 5) Cu—Zn system | 0.18 CuO + 0.078 ZnO | 10.0 | 10.0 | 9.9 | 9.8 |
| 6) Cu—Zn system | 0.11 CuO + 0.049 ZnO | 10.0 | 9.8 | 8.7(1) | 8.3(1) |
| 7) Cu—Zn system | 0.049 CuO + 0.021 ZnO | 9.9 | 8.6(1) | 5.6(4) | 2.6 |
| 8) Untreated Controls | 0.0000 | 9.2 | 0.6 | 0.0 | 0.0 |
| Average Termite Ratings of Cu and Cu—Zn Preservative Treated Wood Stakes installed in Gainesville, FL | | | | | |
| 1) Cu alone System | 0.065 CuO | 10.0 | 6.6(2) | 4.2(5) | 3.4 |
| 2) Cu alone System | 0.12 CuO | 9.9 | 8.9 | 7.0(2) | 4.1 |
| 3) Cu alone System | 0.19 CuO | 10.0 | 8.5(1) | 8.0(1) | 7.7(1) |
| 4) Cu alone System | 0.25 CuO | 10.0 | 8.4(1) | 8.4(1) | 7.6(1) |
| 5) Cu—Zn system | 0.18 CuO + 0.078 ZnO | 10.0 | 9.7 | 9.6 | 9.4 |
| 6) Cu—Zn system | 0.11 CuO + 0.049 ZnO | 10.0 | 9.4 | 8.9 | 7.6(1) |
| 7) Cu—Zn system | 0.049 CuO + 0.021 ZnO | 9.7 | 8.1 | 5.7(3) | 2.7 |
| 8) Untreated Controls | 0.0000 | 7.6(1) | 0.0 | 0.0 | 0.0 |

We claim:

1. A composition comprising:

a) a particulate copper or copper compound component;

b) a particulate zinc or zinc compound component;

wherein at least 85 wt % of the particles are in the range of from .001 to 25 microns; and c) a polymeric dispersant, wherein the weight ratio of elemental copper to elemental zinc is in the range of from 15:1 to 1:15.

2. The composition of claim 1, wherein the weight ratio of elemental copper to elemental zinc is in the range of from 5:1 to 1:5.

3. The composition of claim 1, wherein the composition comprises at least one of the following copper compounds: copper hydroxide, cupric and/or cuprous oxide, and copper carbonate.

4. The composition of claim 2, wherein the composition comprises at least one of the following copper compounds: copper hydroxide, cupric and/or cuprous oxide, and copper carbonate.

5. The composition of claim 1, wherein between 50 wt % to 90 wt % of the particles have a diameter in the range of from 0.001 to 25 microns.

6. A method of preserving wood comprising the steps of:
   a) applying to the wood a composition comprising:
      1) a particulate copper or copper compound component; and
      2) a particulate zinc or zinc compound component;
      wherein at least 85 wt % of the particles are in the range of from 0.001 to 25 microns; and
   b) impregnating the wood with said particles such that the particulate copper or copper compound component is present at a wood retention in the range of from 0.005 to 1 pounds per cubic foot (pcf) CuO equivalents, and the particulate zinc or zinc compounds are present at a wood retention in the range of from 0.005 to 1 pounds per cubic foot (pcf) ZnO equivalents.

7. The method of claim 6, wherein the weight ratio of elemental copper to elemental zinc in the composition is in the range of from 15:1 to 1:15.

8. The method of claim 6, wherein the weight ratio of elemental copper to elemental zinc in the composition is in the range of from 5:1 to 1:5.

9. The method of claim 6, wherein the composition comprises at least one of the following copper compounds: copper hydroxide, cupric and/or cuprous oxide, and copper carbonate.

10. The method of claim 8, wherein the composition comprises at least one of the following copper compounds: copper hydroxide, cupric and/or cuprous oxide, and copper carbonate.

11. The method of claim 6, wherein between 50 wt % to 90 wt % of the particles in the composition have a diameter in the range of 0.001 to 25 microns.

12. The method of claim 6, wherein the composition applied to the wood further comprises an azole.

13. The method of claim 12, wherein the azole is tebuconazole.

14. Wood comprising:
   1) a particulate copper or copper compound component; and
   2) a particulate zinc or zinc compound component;
   wherein at least 85 wt % of the particles are in the range of from 0.001 to 25 microns, such that the particulate copper or copper compound component is present at a wood retention in the range of from 0.005 to 1 pounds per cubic foot (pcf) CuO equivalents, and the particulate zinc or zinc compounds are present at a wood retention in the range of from 0.005 to 1 pounds per cubic food (pcf) ZnO equivalents.

15. Wood of claim 14, wherein the weight ratio of elemental copper to elemental zinc in the wood is in the range of from 15:1 to 1:15.

16. Wood of claim 14, wherein the weight ratio of elemental copper to elemental zinc in the wood is in the range of from 5:1 to 1:5.

17. Wood of claim 14, wherein the particular copper or copper compound component comprises at least one of the following copper compounds: copper hydroxide, cupric and/or cuprous oxide, and copper carbonate.

18. Wood of claim 16, wherein the particular copper or copper compound component comprises at least one of the following copper compounds: copper hydroxide, cupric and/or cuprous oxide, and copper carbonate.

19. Wood of claim 14, wherein between 50 wt % to 90 wt % of the particles in the wood have a diameter in the range of from 0.001 to 25 microns.

20. Wood of claim 14 further comprising an azole.

21. Wood of claim 20, wherein the azole is tebuconazole.

* * * * *